United States Patent [19]

Constant

[11] Patent Number: 5,793,216
[45] Date of Patent: Aug. 11, 1998

[54] MULTIPHASE FLOWMETER

[75] Inventor: Michel Constant, Saint Denis, France

[73] Assignee: Institut Francais du Petrole, Rueil-Malmaison, France

[21] Appl. No.: 476,575

[22] Filed: Jun. 7, 1995

[30] Foreign Application Priority Data

| Jul. 8, 1994 | [FR] | France | 94 08502 |
| Oct. 20, 1994 | [FR] | France | 94 15455 |

[51] Int. Cl.[6] ................................. G01N 22/04
[52] U.S. Cl. ........................ 324/639; 324/640
[58] Field of Search ................. 324/637, 639, 324/640, 641; 73/61.44, 861.04, 861.08, 861.11, 61.41

[56] References Cited

U.S. PATENT DOCUMENTS

| 4,423,623 | 1/1984 | Ho et al. | 324/639 |
| 4,486,714 | 12/1984 | Davis, Jr. et al. | 324/639 |
| 4,764,718 | 8/1988 | Revus et al. | 324/640 |
| 4,788,852 | 12/1988 | Martin et al. | 73/61.44 |
| 4,812,739 | 3/1989 | Swanson | 324/640 |
| 4,888,547 | 12/1989 | McGinn et al. | 324/637 |
| 5,049,823 | 9/1991 | Castel et al. | 324/640 |
| 5,101,164 | 3/1992 | Marrelli | 73/61.44 |
| 5,107,219 | 4/1992 | Marrelli et al. | 324/640 |
| 5,150,061 | 9/1992 | Csatel et al. | 324/640 |
| 5,157,339 | 10/1992 | Scott et al. | 324/640 |
| 5,485,743 | 1/1996 | Taherian et al. | 324/637 |
| 5,502,339 | 3/1996 | Yamaguchi et al. | 324/639 |

FOREIGN PATENT DOCUMENTS 0 399 876  11/1990  European Pat. Off. .

*Primary Examiner*—Vinh P. Nguyen
*Attorney, Agent, or Firm*—Antonelli, Terry, Stout & Kraus, LLP

[57] ABSTRACT

A device and method for determining the proportion of the phases of a multiphase fluid is disclosed. The device includes microwave emission and reception devices which are suited to the composition variation of the multiphase fluid, a processor and control for determining directly, from measurements of amplitude and phase shift of a beam crossing the multiphase medium and a rate of occupation of liquid phase and/or a gas phase for a given section of the pipe. The flow rate of each of the phases is determined.

19 Claims, 4 Drawing Sheets

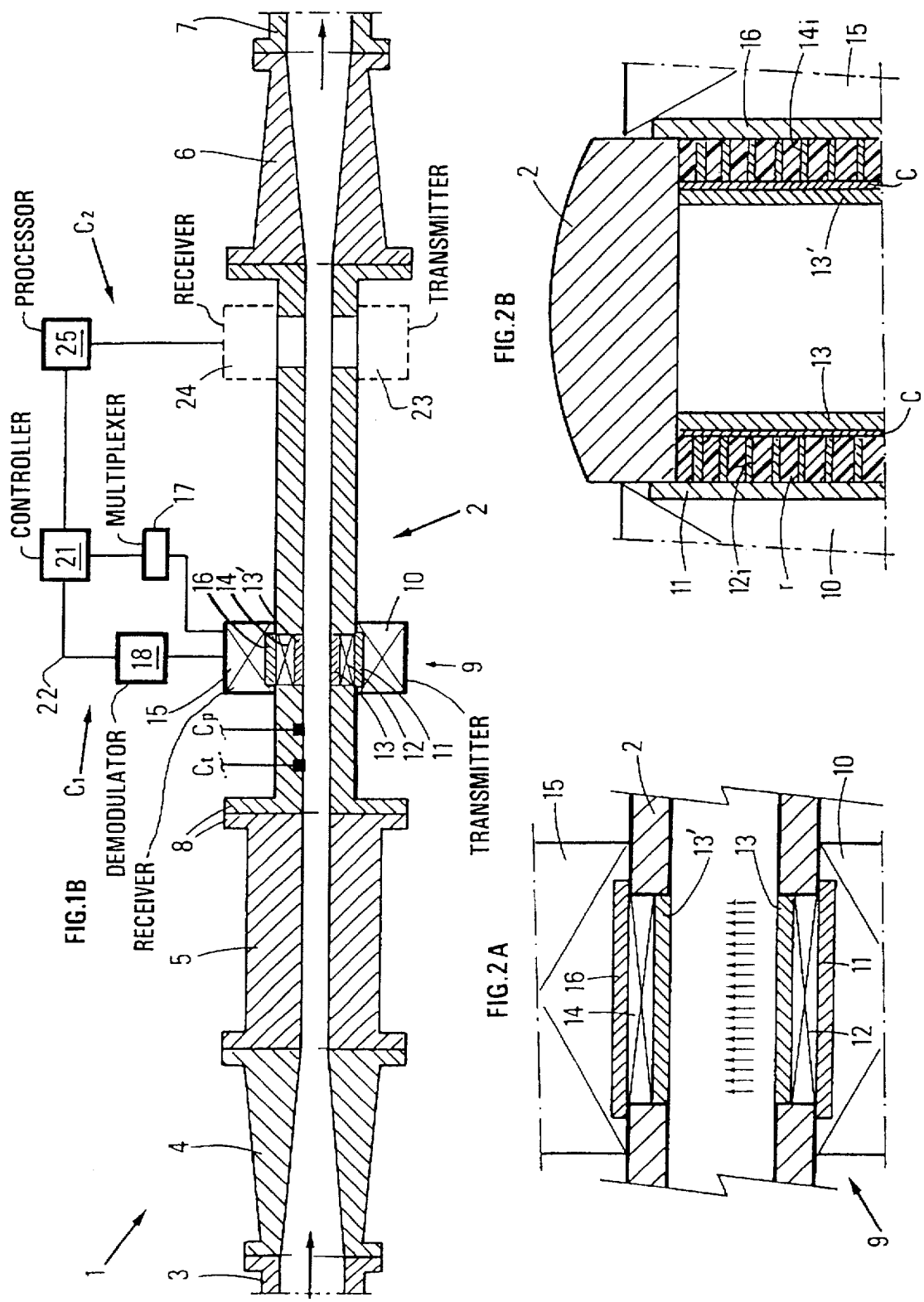

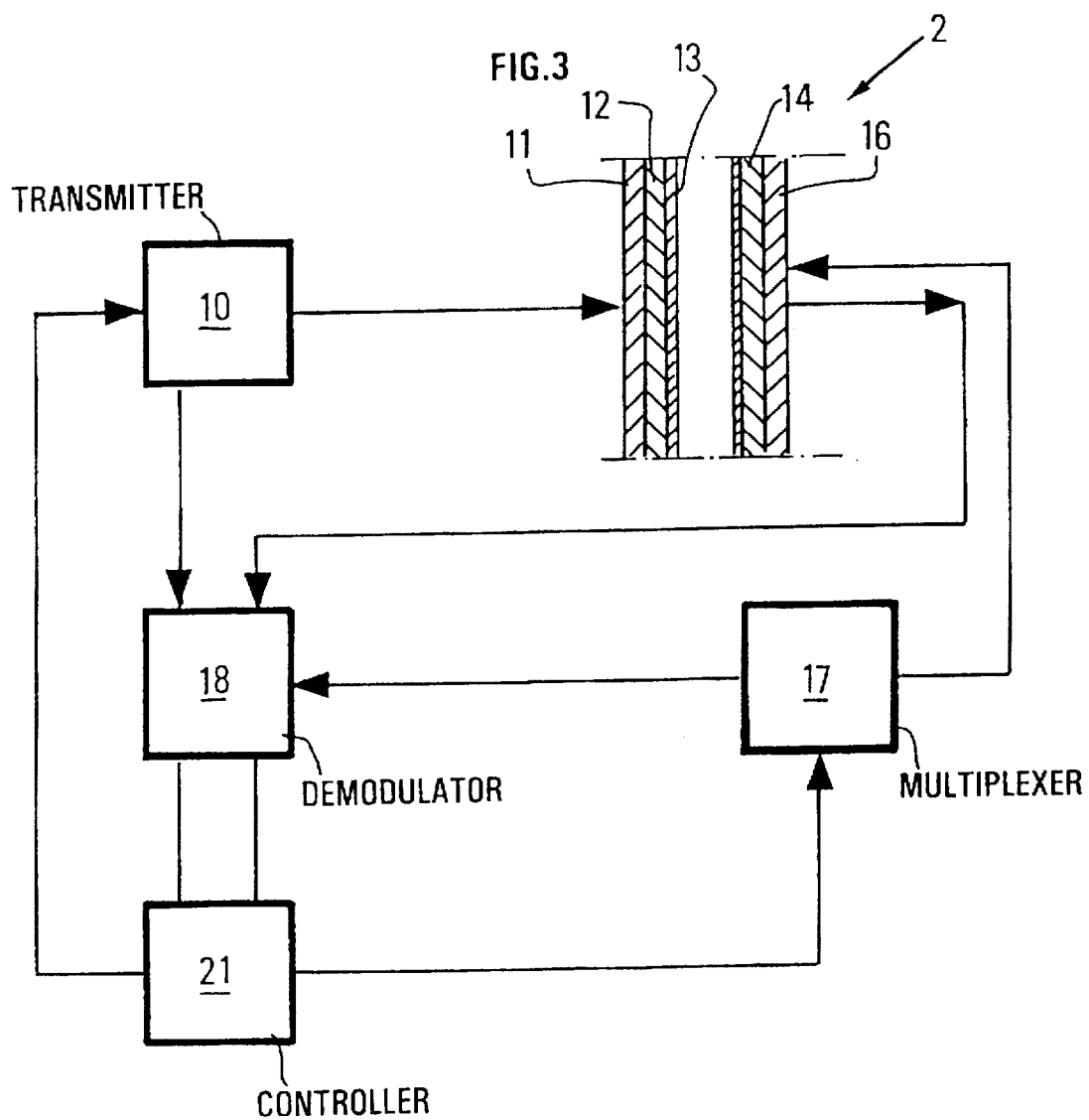

MULTIPHASE FLOWMETER

BACKGROUND OF THE INVENTION

1. Field of the Invention

The present invention relates to a method and to a device for determining the proportion and nature of the different phases constituting a multiphase with each phase having at least one intrinsic characteristic allowing them to be discriminated.

2. Description of the Prior Art

There are already well-known devices which utilize a low frequency electric field and which allow a mapping of the medium to be achieved by means of capacitance or conductance measurements of a multiphase medium. However, devices of this type present many drawbacks such as the conductivity of the medium, inter-electrode leakage, the formation of a wall film in some cases, wettability problems, which can decrease the reliability and the simplicity of the measurements that are desirable within the scope of an industrial application.

The devices based on the use of gamma rays or of X rays have lower sensitivities than the devices using electromagnetic waves, and they are also heavier methods to implement.

Other imagery devices use nuclear magnetic resonance. They allow independent measurements of the proportion and of the flow rate of water and of oil to be performed, for example, but on the other hand they present space, weight and response time problems, so that these devices are not compatible with the constraints of the petroleum industry.

French Patent 2,647,549 of the Assignee describes a device and a method using microwave beams for determining the average proportion of each of the phases (water, oil or gas) contained in a multiphase effluent flowing in a pipe.

From the teachings contained in U.S. Pat. Nos. 4,812,739 and 4,820,970, it is well-known to vary the frequency of a microwave beam around the resonant frequency of a phase of a multiphase fluid and to determine the proportion of this phase by measuring the attenuation of the wave that has crossed the fluid, but not the proportion of all the phases contained in this fluid. Furthermore, these patents do not describe wave emission and reception devices perfectly adaptable to the composition variation of a multiphase fluid, and especially to the permittivity variation of the fluid in time.

SUMMARY OF THE INVENTION

The invention is particularly well-suited for determining the proportion of each phase constituting a multiphase fluid comprising several phases each having a permittivity value depending on its nature and at least two of the permittivity values allowing the phases to be discriminated.

The object of the present invention applies advantageously, but nonexclusively, to the determination of the rate of occupation or of the proportion of the phases constituting a petroleum effluent, such as an aqueous phase, an organic phase and a gas phase, and to a mapping of this effluent, for a given section of a pipe in which it circulates.

The petroleum effluent can also contain a solid phase, for example, sand particles, hydrate crystals, asphaltenes or other heterogeneities.

The knowledge of the quantities of each of the phases of a petroleum effluent and particularly the precise knowledge of the water, oil and gas flow rates measured simultaneously at the outlet of a petroleum production well is necessary, notably in reservoir engineering for the control and the safety of the production of each well, and during development, for the follow-up of the production and the protection of the collecting system transferring the crude effluents towards a separation and/or processing center.

Another example of an application of the invention relates to the transportation of multiphase petroleum effluents without phase separation, using pumping devices whose optimum running can depend at any time on the composition of the effluents, and more particularly, on its average liquid rate and its gas/liquid volumetric ratio.

Multiphase fluid or petroleum effluent flows have many regime patterns, which are quickly variable and which require fast measurement devices and processes suited notably to this type of flow.

The invention can also be applied in any other field in which it is useful to know, in a nondestructive way, the proportion and the distribution of dicriminable and immiscible phases constituting a multiphase medium.

The invention can also be applied to determine the proportion of a phase present in a multiphase medium which can comprise several phases having different natures which are discernable from one another by at least one parameter.

The present invention overcomes the above-mentioned drawbacks and improves the measuring accuracy of devices in this field. It notably allows determination precisely of the nature and the proportion of each phase included in a multiphase fluid, especially the proportion of the phases contained in a petroleum type effluent flowing for example in a pipe safely for the operating staff.

The use of specific antennas notably allows analysis of a multiphase fluid whose composition varies in time, and this variation can notably be identified by means of a parameter such as the permittivity.

Furthermore, the invention allows fast, nearly real time measurements to be performed, i.e. the measuring time is short in relation to the spatial and temporal variations or instabilities of the structure of the multiphase fluids.

In the description hereafter, "optimizing an antenna" refers to the optimization of the transmission of the electromagnetic field of the antenna to the multiphase medium.

Furthermore, the expression "multi-element antenna" designates an antenna comprising several elements.

The present invention relates to a method for determining the proportion of at least one phase constituting a part of a multiphase medium comprising at least a liquid phase and at least a gas phase, the phases having at least one characteristic allowing them to be discriminated.

The method can comprise at least a measuring cycle defined by the stages as follows:

a) the multiphase medium is irradiated with an electromagnetic field coming from a first emission source, the field having a frequency value fe;

b) the value of the amplitude Aei and of the phase shift Phei of the electromagnetic field that has crossed the medium is measured at at least one elevation Pi fixed with respect to the multiphase medium; and c) the proportion of each of the liquid and/or gas phases is determined for at least one elevation Pi from the amplitude and phase shift measurements obtained in stage b), from data previously stored in a processor and from the associated frequency value.

The frequency value of the electromagnetic field can be varied from fe to a frequency fe+1, and stages a) to c) are repeated.

The characteristic discriminating the different phases with microwaves can be the permittivity.

With a multiphase medium flowing in a pipe of a given section, the measuring cycle comprising stage a) to c) can be carried one or several times and at different points, and the distribution and the proportion of at least one phase can be determined therefrom for a section of the pipe defined by the direction of the electromagnetic field and one side of the pipe having a nonparallel direction with respect to the direction of propagation of the microwave beam.

A transmitting antenna comprising several elements and a receiving antenna comprising several elements can be used, and stage a) is performed by irradiating the medium from all the elements of the transmitting antenna, then stage b) is performed by scanning all the elements of the receiving antenna one after the other.

A transmitting antenna comprising several elements and a receiving antenna comprising several elements can be used, and stage a) can be performed by irradiating the medium from an element of the transmitting antenna, then stage b) can be performed by scanning the corresponding element of the receiving antenna, and this operation can be repeated for all the elements of the transmitting antenna and of the receiving antenna.

A transmitting antenna comprising several elements and a receiving antenna comprising several elements can be used, and stage a) can be performed by irradiating the medium from an element of the transmitting antenna, then stage b) can be performed by scanning all the elements of the receiving antenna one after the other.

The previously stored data of stage c) can be determined from a multiphase fluid whose phases, nature and proportion are known.

The multiphase medium can be irradiated with a microwave beam whose frequency preferably ranges between 2 and 8 GHz.

It is possible to measure the velocity of at least one phase such as the liquid phase and/or the gas phase and/or the solid phase contained in the multiphase medium by Doppler effect by irradiating the multiphase medium by means of an electromagnetic field and/or of an ultrasonic wave, and the flow rate of the phase or of each of the phases can be determined.

The invention further relates to a device for determining the proportion of at least one phase contained in a multiphase medium, the multiphase medium comprising at least a liquid phase and at least a gas phase, the medium circulating in a pipe of known section, comprising in combination at least one means of emission of an electromagnetic field, such as a microwave beam, at least one means of reception of the electromagnetic field that has crossed the multiphase medium, and a processing and control means for determining directly, from amplitude and phase shift measurements of the electromagnetic field that has crossed the multiphase medium, the rate of occupation of the liquid phase and/or of the gas phase for a given section of the pipe.

The emission and reception elements can be wide band antennas comprising several radiant elements, the elements being separated from one another by a first material and the device can comprise a second material (c) located between the antennas and a microwave-transparent window of the pipe, the first and second materials having dielectric characteristics allowing the antennas to be optimized to a relative permittivity variation of the multiphase medium.

The first material can be an epoxy resin and the second material a ceramic suited for withstanding a temperature at least equal to 100° C. and a pressure varying at least up to 100 bars.

The device can comprise a device for measuring the velocity of at least one phase of the multiphase medium.

The application of the method and of the device can relate to the determination of the proportion of the phases constituting a petroleum effluent.

The present invention thus affords many advantages in relation to the processes commonly used in the prior art. In fact, the microwave radiation provides a safe use for the staff and requires a smaller staff for operating the device, in comparison with the devices using gamma or X rays or emissions of neutrons. Furthermore, the components used in the device have a weight and a size compatible with the mobility required for such a type of device used in the petroleum field.

The use of microwave radiations of short wavelength, in the millimeters range for example, allows obtaining of an accurate image of the distribution of the different phases and increasing the measuring accuracy. The definition of the nature and of the quantity of the phases is improved by carrying out measurements for different frequency values.

Besides, the frequency range used leads to an inexpensive device.

Another advantage of the device comes from the use of antennas specially optimized to the temporal variation of the structure of a multiphase fluid, therefore to its composition and notably to its dielectric permittivity. They are also designed so as to minimize the leaks that appear when the beam crosses the microwave-transparent walls of the pipe such as windows.

Besides, the possible use of a synchronous detection device improves the measuring accuracy.

The device is also particularly well-suited for withstanding attacks from the multiphase fluid with which it is in contact, such as the chemical attacks due to the nature of the petroleum effluents.

BRIEF DESCRIPTION OF THE DRAWINGS

Other features and advantages of the present invention will be clear from reading the description hereafter, given by way of non limitative examples, with reference to the accompanying drawings in which:

FIGS. 1A and 1B respectively show a perspective view of a device according to the invention and its associated flowsheet;

FIGS. 2A and 2B show details of the antennas and their arrangement;

FIG. 3 shows an example of layout of the elements making up the signal control and processing device according to the invention;

DESCRIPTION OF THE PREFERRED EMBODIMENTS

The examples given hereafter notably allow determination of the proportion of the phases constituting a multiphase type petroleum effluent circulating in a pipe. The phases to be discriminated and whose proportion is sought are for example an aqueous phase such as water or brine, an organic phase such as oil and a gas phase mainly made up of methane whose relative permittivity values respectively are in the following ranges: 6–100; 2–3; and about 1. The permittivity variation is very high between the water and the oil or the gas, whereas the permittivity variation between the gas and the oil is relatively low.

The brine is for example water containing a quantity of salt ranging between 0 and 300 g/l, preferably between 0 and 100 g/l of salt.

The effluent can possibly comprise a solid phase for example in the form of solid particles, sand or hydrates for example.

In the example described hereunder, during propagation of a medium consisting of several phases, such as a multiphase fluid, a beam of electromagnetic energy or electromagnetic field, for example microwaves, are reflected and diffracted at least partly when encountering a discontinuity, which may be a permittivity or conductivity value variation resulting from the difference of the phases.

A data table is formed from the measurement of the amplitude and phase shift values of the microwaves diffracted by the discontinuities or heterogeneities encountered, the nature of the different phases is determined and the proportion of each phase contained in the multiphase fluid is determined.

The electromagnetic beam advantageously has a low energy, of the order of a few mW.

A measurement of the velocity of each of the phases, combined with the determination of the rate of occupation of the phases included in the multiphase fluid, leads to the value of the volume flow rate of each of the phases.

Figure 1A:
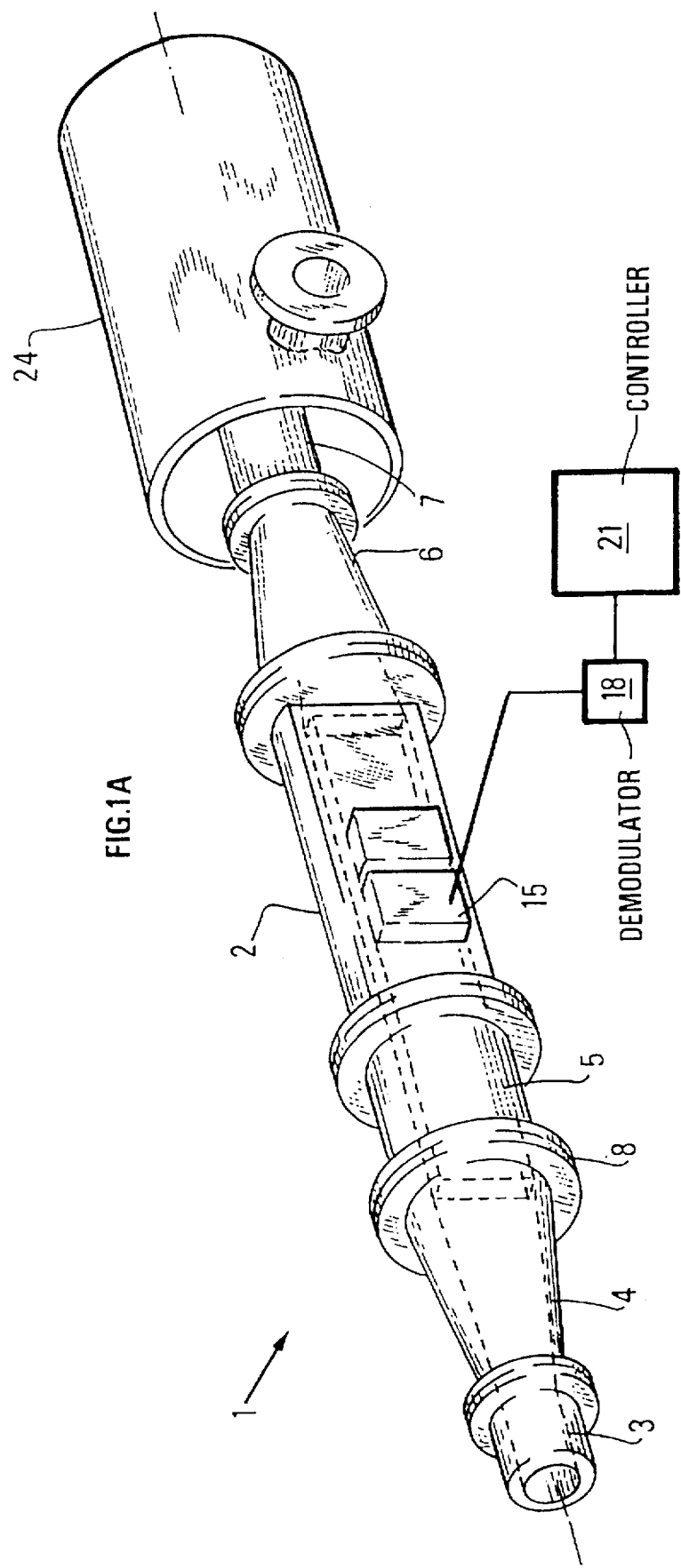

The device shown in FIGS. 1A and 1B comprises a measuring section 1 in which the multiphase fluid, for example a petroleum effluent comprising water or brine, oil and gas, circulates. Section 1 comprises several elements connected to one another, among which a measuring element 2 of rectangular shape equipped with devices necessary to the measurement described hereafter. The effluent flows in through a pipe 3, passes through a fist adaptation element 4 having a suitable shape so that the flow change from a cylindrical section to a rectangular section occurs with a minimum amount of disturbances, and through a damping element 5 that damps the turbulences generated during the change from a cylindrical to a rectangular cross section. Prior to passing from the measuring element 2 into a discharge pipe 7, the effluent passes through a second adaptation element 6 whose purpose is to adapt the flow coming from measuring element 2 to the geometry of the effluent discharge pipe 7. The different elements 2, 3, 4, 5, 6 and 7 are connected together for example by flanges 8 commonly used in the petroleum field, whose main function is to provide a seal between the various elements.

Advantageously, the rectangular shape of the measuring element 2 tends to stratification of most of the circulating multiphase fluids, and such flows thus take the form of several layers each being one of the phases of the fluid. Such a flow pattern facilitates measurements and therefore the mapping of the flow.

Advantageously, measuring element 2 is equipped with temperature Ct and pressure Cp detectors located for example at the inlet of the measuring section. These detectors measure the thermodynamic conditions under which the data are acquired in order to permit performing of error corrections.

The device shown in FIG. 1B comprises a measurement chain $C_1$ whose purpose is to qualify and to quantity the different phases constituting the multiphase effluent, i.e. to know their nature and proportion.

It comprises for example:

an emission block 9 for emitting an electromagnetic field such as a microwave beam, integral with measuring element 2, comprising for example a source of microwaves 10, a device 11 whose function is to transmit to a transmitting antenna 12 (FIGS. 2A and 2B) comprising for example of several elements 12$i$ an equi-amplitude and equal phase beam so that all the elements 12$i$ of antenna 12 radiate a substantially uniform and homogeneous field, a microwave-transparent window 13 located substantially in line with the emission antenna 12. The microwave beam generated by source 10 is transmitted to the multiphase effluent through window 13 and then crosses the petroleum fluid in which it is at least partly diffracted by the heterogeneities contained therein. A reception block 15 located after a window 13' of the same type as window 13 receives the field resulting from the initial field that has crossed the effluent without being disturbed and from the part of the field diffracted by the impurities or heterogeneities included in the effluent. This reception block comprises for example a receiving antenna 14 comprising for example several antenna elements 14$i$ (FIGS. 2A and 2B) and a device 16 located downstream from antenna 14, whose purpose is produce a signal representative of the resulting electromagnetic field received by each antenna element 14$i$.

The transmitting and receiving antennas 12 and 14 are for example connected respectively to the devices 11 and 16 by semirigid cylindrical waveguides for example, working within a frequency range between 1 to 10 GHz, preferably between 2 and 8 GHz.

Device 16 is connected to a multiplexer 17 that controls switches (not shown) included in device 16 for scanning the different antenna elements 14$i$, and to a demodulation set 18 of a known type suited for delivering low frequency signals to a processing and control device 21 connected to the demodulation set by conventional electric links 22. The rate of scanning of the different antenna elements 14$i$ given by device 21 is preferably selected quickly in relation to the velocity of flow of the multiphase effluent.

The processing and control device 21 can be connected to the module 18 by an optocoupled link.

The device 21 is for example a microcontroller whose function is to receive and process the data. It also processes sequences of the method according to the invention, notably by controlling most of the devices described above and the microwave emission source.

The demodulation device 18 can advantageously comprise a synchronous detector for improving the signal-to-noise ratio. In this case, multiplexer 17 can comprise an internal generator that delivers the signal allowing the effective signal to be modulated.

Windows 13 and 13' are preferably made from a material having a low attenuation coefficient for the frequencies used, and protect the antennas from any type of attacks, notably the chemical attacks of the petroleum fluid. The transparent window 13 can be made of PVDF, which withstands methane and $H_2S$ well for example.

It is possible to connect microcontroller 21 to the other elements by means of a flexible cable whose electric and physical characteristics are such that they allow the processing assembly to be shifted with respect to the measuring section. The image of the phase distribution can thus be easily presented to a user on the microcontroller screen.

An example of control of the electronic and computer circuits described in connection with FIGS. 1B, 2B and 3 comprises for example the stages as follows:

microcontroller 21 starts the operations by sending:

an emission command to the microwave emission source 10 which generates a microwave beam of frequency Fe at the various elements 12$i$ of the transmitting antenna 12 simultaneously;

immediately thereafter, it delivers a signal to multiplexer 17 at a selected frequency, for example equal to 200 KHz, in order to activate the switches of device 16 so as to scan the elements 14$i$ of the receiving antenna; and the demodulation set 18 also receives a reference signal coming from the emission source.

From the reference signal and from the signals received by elements 14$i$ of the receiving antenna 14, the demodulation set 18 generates two low frequency signals corresponding respectively to the amplitude Aei of the diffracted field received by an entenna element 14$i$ and the value of the phase shift PHei of the diffracted field received by this element. These values are given for a frequency value Fe of the source of microwaves.

Each antenna element 14$i$ is for example located, according to the height of the measuring section, by an elevation Pi, taken for example with respect to the lower part of the measuring section, with which a couple of values Aei and PHei of the diffracted field is associated, i.e. the nature and the quantity of the phase corresponding to this elevation.

The two signals Aei and PHei representative of the diffracted field received by an antenna element 14$i$ are thereafter transmitted to the microcontroller and stored therein, for example in the form of a data table comprising couples of values [(Aei, PHei, Pi) Fe] where Fe is the emission frequency.

In order to improve the measuring accuracy, it is possible to measure the amplitude and phase shift values for several frequency values Fe. In this case, at the end of a measuring cycle performed at a frequency Fe as described above, the microcontroller sets the frequency value to a new value Fe+1 and starts a new cycle of acquisition, measurement and storage of the new data A(e+1)i, PH(e+1)i, for all the antenna elements 14$i$ of elevation Pi.

Tests allow preferred frequency bands to be chosen allowing the discrimination of the three phases, gas, oil and water, to be optimized.

The following four frequency bands will thus be preferably used:
Band $F_1$=2.1 GHz to 2.4 GHz,
Band $F_2$=2.6 GHz to 3.15 GHz,
Band $F_3$=3.7 GHz to 4 GHz,
Band $F_4$=6.1 GHz to 6.3 GHz.

The following four values are preferably selected within these four frequency bands:
$F_1$ close to 2.6 GHz, $F_2 \approx 3$ GHz, $F_3 \approx 3.8$ GHz and $F_4 \approx 6.1$ GHz.

The frequency values selected above notably allow:

obtaining a response of the receiving antenna that is substantially uniform in amplitude and in phase when the pipe is practically entirely filled with one of the three phases;

the frequency selected substantially equal to 2.6 GHz is particularly well-suited to fluids having a high salinity value and the signal attenuation being high in such effluents, the noise is preferably minimized by using low frequencies;

frequency $F_1$ also has the advantage of allowing an amplitude discrimination of the two phases gas and oil; and frequencies $F_2$, $F_3$ and $F_4$ allow a homogeneous response to be obtained for all the phases.

The data can for example come in the form of digitized dot matrices.

By means of appropriate software that takes into account the temperature and pressure values measured by detectors Cp and Ct, the microcontroller 21 processes the data and determined therefrom the proportion of each phase present in the effluent, and this proportion can be determined for a place or a zone of the section, this place or zone of the section can be a portion whose height is substantially equal to the width of an antenna element 14$i$ and whose width is substantially equal to the depth of the section. This processing can be carried out in different ways, among which those described hereafter.

The processing can comprise a stage during which, from the data tables obtained and previously stored, and from tables obtained during prior tests, the measured data and the data previously obtained is compared in order to determine therefrom the nature and the quantity of a phase corresponding to an elevation Pi.

In another embodiment example, the processing uses threshold values determined for example from measured histograms and a law of behaviour of the amplitude and phase variations of the signal obtained as a function of the frequency, in order to determine therefrom the nature of each phase and their relative proportions.

The threshold values for the amplitude and the phase are calculated at 10% and 90% of the integral of the histograms achieved in the tests.

It can also implement a data classification method using neural networks.

A phase distribution image can be obtained from the analysis of the signal obtained by all the elements 14$i$ of the receiving antenna in order to obtain information on the distribution of the phases in the direction of propagation of the wave, which corresponds to determining the phase distribution according to the depth of the measuring section, and over the height of the section. The amplitude and the phase of all the signals received are analyzed and tomography algorithms are for example used.

Tests carried out on a petroleum effluent comprising an oil phase, water, and gas, with a stratified type flow structure, i.e. the different phases have the form of strata in the pipe and are arranged according to their density, have allowed obtaining the high and low threshold values for determining the amplitude and the phase grouped together in the table hereafter.

| Fluid | Frequency MHz | Amplitude dB | Phase |
|---|---|---|---|
| Oil | 2687 | −4.5 < A < 0.5 | −22 < P < 13 |
|  | 3053 | −10 < A < 3 | −60 < P < 28 |
|  | 3832 | −2.5 < A < 1 | −26 < P < 5 |
|  | 6122 | −6 < A < 2 | −20 < P < 18 |
| Water | 2687 | −7 < A < −1 | −60 < P < −18 |
|  | 3053 | −10 < A < ' | −128 < P < −240 |
|  | 3832 | −5 < A < 0.5 | −114 < P < −70 |
|  | 6122 | −8 < A < 1.5 | −144 < P < −200 |
| Gas | 2687 | −8 < A < −16 | I < P < Indeterminate |
|  | 3053 | −45 < A < −19,5 | I < P < I |
|  | 3832 | −8 < A < −17,5 | I < P < I |
|  | 6122 | −46 < A < −17,5 | I < P < I |

The data stored previously may have been obtained from a fluid of known composition and under given pressure and temperature conditions.

Advantageously, and without departing from the scope of the invention, it is possible to improve the measuring accuracy for example by proceeding as follows: an element 12$i$ of the transmitting antenna is activated and the corresponding element 14$i$ of the receiving antenna is scanned simultaneously. All the couples (12$i$, 14$i$) of the transmitting and receiving antenna elements are thus scanned.

It is also possible to proceed in the following way: an element 12$i$ of the transmitting antenna is activated and then radiates then the electromagnetic field, and all or part of the elements 14$i$ of the receiving antenna are scanned in order to measure the diffracted signal. The antenna elements 14$i$ can be scanned all at the same time or individually one after the other.

Such measurements provide additional information representative of the physical phenomenon and allow for example, by using appropriate processing algorithms, a determination more precisely of the quantity of each of the phases obtained, for example by imagery.

FIGS. 2A and 2B show in detail the antennas used in the device according to the invention and their layout with respect to the measuring section. The design of these antennas, as well as the selection of the material from which they are made, allow them to work within a wide frequency range, preferably between 2 and 8 GHz.

They are suited to a petroleum effluent of variable relative permittivity value, for example between 1 and 300 and preferably between 1 and 100.

The antennas 12 and 14 of FIGS. 2A and 2B comprise for example 32 elements 12$i$ and 32 elements 14$i$ placed one beside the other and separated by a material r such as an epoxy resin, used for fitting these elements together and for ensuring their resistance to relatively high pressure values, for example greater than 100 bars, and temperatures that can be at least equal to 100° C. The relative permittivity value of this resin can be substantially equal to 4 and it can be a CW 1991 BO/HY 2954BD type commercial resin marketed by CIBA.

The radiant surface of transmitting antenna 12 is applied to the microwave-transparent window and radiates, from all its antenna elements 12$i$, a homogeneous and substantially uniform microwave field over the major part of the emission surface.

It is possible to place between transmitting antenna 12 and window 13 a material c such as a ceramic, selected for optimizing the energy and phase transmission of the microwave beam that can range for example between 2 and 8 GHz, and for ensuring thereby a maximum penetration of the beam into the petroleum effluent.

Advantageously, the relative permittivity value of the ceramic is substantially equal to 30 and selected as a function of the maximum and minimum values of the relative permittivity of the petroleum effluent.

In another embodiment, not shown, antennas 12 and 14 consist for example of a linear retina such as that described in French Patent 2,635,187 of the SATIMO company. This retina is integral with a microstrip type flat antenna whose material is selected as a function of the criteria stated above for multi-element antennas.

The sensitivity of the multi-element antennas 12 and 14 of FIGS. 2A and 2B is higher than that of the above-mentioned antennas comprising a linear retina. The pitch or distance between the elements 12$i$ and 14$i$ of the transmitting and receiving antennas is fixed for example as a function of the space resolution desired for the device, i.e. the distance between the measuring points of the field diffracted by the heterogeneities.

In another embodiment, the device according to the invention allows determination of the velocity of flow for each phase circulating in the pipe.

A measurement chain $C_2$ (FIG. 1B) suited for velocity measurements can advantageously complete the measuring device. It is for example located downstream from the phase quantification measurement chain $C_1$.

It comprises for example a radiation emission device 23, a reception device 24 for receiving the wave that has crossed the multiphase effluent, this reception device 24 being connected to a signal processing device 25 that itself is connected to microcontroller 21. The elements are connected together by electric links identical to links 22.

The signal reception 24 and processing 25 devices are for example similar to the devices described in French Patent Application 94/08,380 filed by the assignee, which allows measuring velocity of a multiphase effluent circulating in a pipe, for example over a height of the measuring section.

Another way of proceeding is in measuring, by means of an appropriate device, the velocity by Doppler effect, as it is known.

The radiation emission device can comprise a source of electromagnetic waves such as microwaves, or of pressure waves such as acoustic waves.

Such a measurement chain $C_2$ allows determination selectively of the value of the phase velocity associated with a point in the pipe. This information is then transmitted to the microcontroller which integrates it at the level of the signal processing so as to associate a velocity value with a phase whose nature has been characterized by following, for example, the stages of the method described in connection with FIGS. 1A, 1B and 3. From the value of the velocity and of the nature of the phase, the flow rate associated with a phase of the multiphase effluent is determined by means of an appropriate software module, at different points of the pipe.

An associated density measurement allows determination of the value of the mass flow rate of each of the phases.

According to an advantageous embodiment of the invention, a velocity measurement is performed for each of the phases of the petroleum effluent in order to obtain a precise flow rate value for each one of them.

According to a preferred embodiment described in connection with FIG. 4, a single measurement chain is used for mapping the distribution of the phases of an effluent circulating in the measuring section and simultaneously for performing a velocity measurement by Doppler effect in transmission for each phase.

Figure 4:
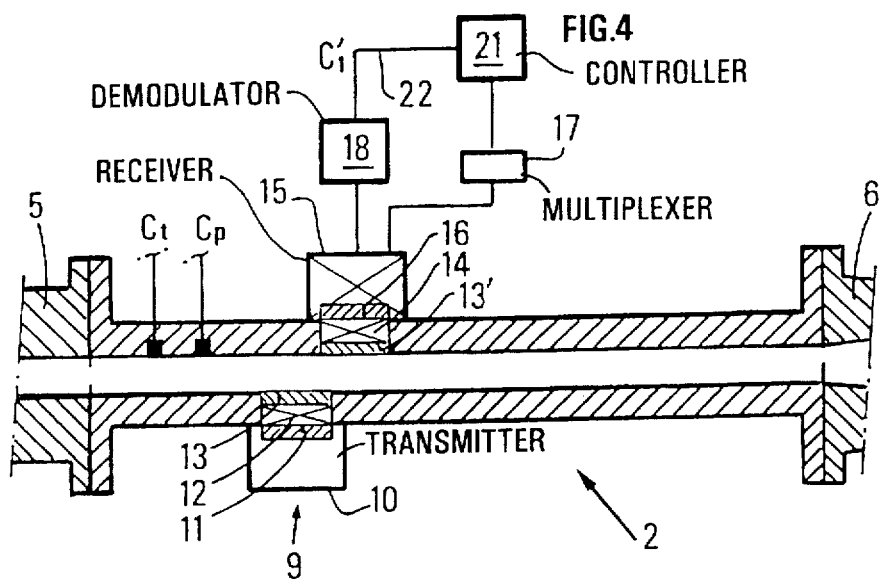
FIG. 4 shows an embodiment comprising a single measurement chain for determining the quantity and the velocity of each phase.

The device described in FIG. 4 differs from the device of FIG. 1B in the layout and the arrangement of the elements of the measurement chain $C_1$ of FIG. 1B. In fact, the transmitting part of chain $C'_1$ comprising all the elements (9, 10, 11, 12 and 13) necessary for the emission of a microwave beam positioned on one side of the measuring section and the part comprising the elements necessary for the reception of the signals (13', 14, 15 and 16) is placed on the other side of the measuring section and shifted with respect to the transmitting part in order to obtain a Doppler signal. Multiplexer 17 and demodulator 18 are connected to microcontroller 21 in a similar way to that described in connection with FIG. 1B, by links 22.

One way of mapping and measuring the velocity of each of the phases of a multiphase effluent differs from one of the procedures described above for the signal processing.

Microcontroller 21 performs an additional stage of processing of the signals coming from demodulator 18 by achieving a spectral analysis of the signals that is well-known to specialists, such as a Doppler spectrum for determining the velocity of each of the phases, water, oil and gas, from the velocity profile obtained over the height of the measuring section. Knowing the nature and the quantity of a phase for a given place of the section of the pipe and the velocity associated with this phase, it is possible to determine the flow rate for each of the phases of the effluent in several places or zones of the pipe, by means of an appropriate software.

This embodiment is particularly advantageous since it uses a single measurement module or chain for determining the quantity and the velocity of a phase, and for determining its flow rate therefrom.

Figure 5:
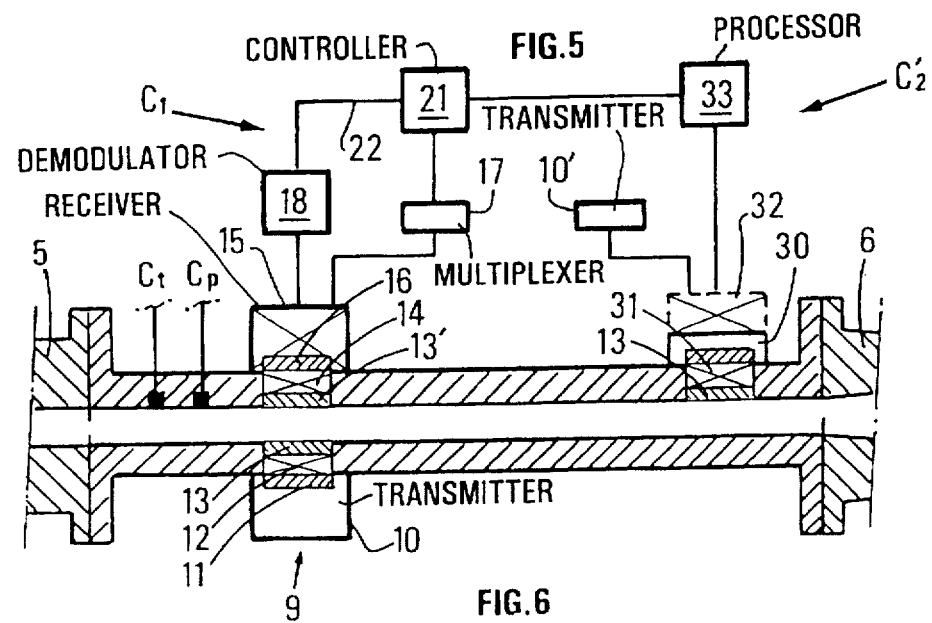
FIG. 5 shows another embodiment comprising a velocity measurement chain using the Doppler effect for reflections located downstream from the first measurement chain.

Another embodiment described in FIG. 5 uses the Doppler effect in reflection for achieving a velocity profile of the multiphase effluent, by using a second measurement chain $C'_2$ located for example downstream from the first measurement chain $C_1$ (FIG. 1B).

Measurement chain $C_2$ comprises emission and reception means 31, for example an antenna whose structure and nature are identical to those of the antennas described in connection with FIGS. 1B, 2A and 2B, this multi-element antenna 31 having the advantage of being able to work to emit as well as to receive.

In this case, the Doppler effect is obtained by tilting the transmitting-receiving antenna 31 at a given angle, for example of the order of 30° to the wall of the measuring section 2.

A second emission source 10' is connected to the transmitting-receiving antenna 31 by means of a multiplexer 30 and to a device 32 such as a circulator whose function is notably to transmit permanently for example the microwave signal coming from the emission source 10' towards an element of the transmitting-receiving antenna 31 and to direct the backscattered signals received by an element of this antenna towards the detection and processing circuits 33.

Microcontroller 21 controls, for example sequentially, the chain for measuring the quantity of each of the phases or mapping chain $C_1$ and the velocity or velocity field measurement chain $C'_2$. It commands notably at the level of measurement chain $C'_2$ the times of emission of the microwaves and the multiplexing of the elements of transmitting-receiving antenna 31.

It also performs a spectral analysis of the signals coming from processing module 33 in order to determine a velocity profile over the height of the pipe and to obtain thereby the value of the velocity associated with a phase of the multiphase effluent. Appropriate software allows for example the Doppler frequency directly proportional to the velocity of the petroleum multiphase effluent to be defined from the Doppler spectrum.

Figure 6:
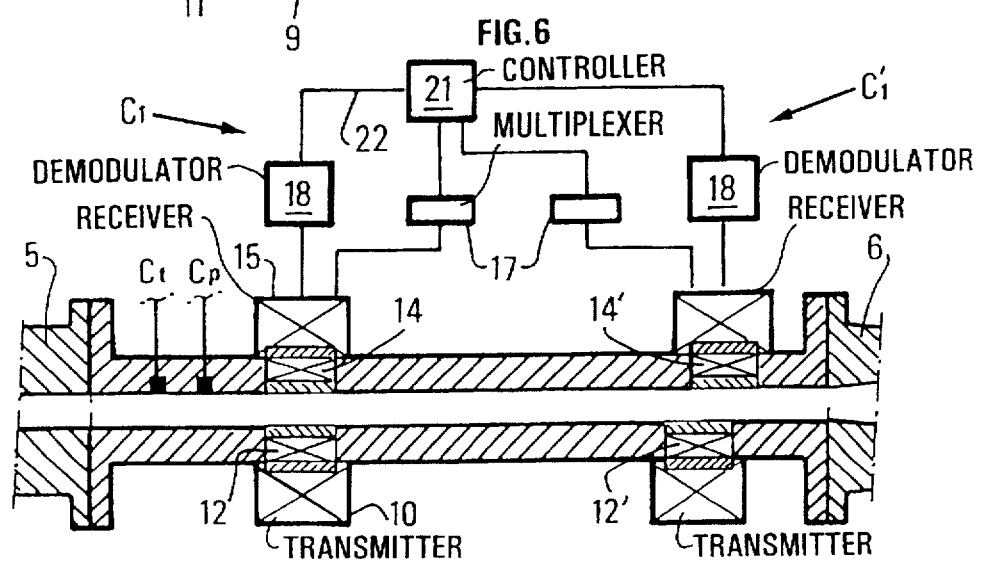
FIG. 6 shows another embodiment comprising two measurement chains using microwaves for determining the quantity of a phase and its velocity.

The device described in connection with FIG. 6 gathers on the measurement element 2 two $C_1$ type measurement chains (FIG. 1B) bearing respectively reference numbers $C_1$ and $C'_1$. The first chain $C_1$ is intended for mapping the multiphase fluid as in FIG. 1B. The receiving antenna 14' of the second chain $C'_1$ is shifted along the axis of the measuring section with respect to the transmitting antenna 12' so as to achieve a velocity measurement or a velocity profile of the multiphase fluid. The two measurement chains are close enough to one another to allow measurements representative of the quantity of a phase and of its associated velocity to be obtained. The implementation of this device variant is identical to that described in connection with FIG. 6, except for the processing of the signal received by the second chain, which uses the Doppler effect in transmission.

The emission and reception devices, the demodulator, the multiplexer and the microcontroller are identical to the devices of FIG. 1B.

Without departing from the scope of the invention, the measuring element 2 can be equipped with two $C_1$ type chains with a distance d between them (not shown in the figures).

The first chain maps the flow at a given time t and the second chain maps the flow at a time t+δt, δt depending on the velocity of flow and on the distance d. A conventional method of crosscorrelation of the signals received by the antenna elements of the first measurement chain and those of the second measurement chain allows to go back to the velocity and to the proportion of each of the phases of the effluent.

The measuring element 2 is advantageously provided with a sealed protective casing, such as a tube 24, protecting the element against outside attacks and also allows it to comply with the safety standards of the petroleum industry.

The measuring section 1 is preferably made from a material unattackable by the petroleum effluent, notably a H2S-corrosion proof material. It can comprise a material absorptive to high frequencies, not shown, located in its lower part, and/or in its upper part which allows minimizing the antenna edge spurious radiations and thereby to increase the measuring accuracy and the quality of the digitized image of the lower part and of the upper part of the section, the image being obtained from the data of the table.

Without departing from the scope of the invention, the frequency-varying source can be replaced by a plurality of sources emitting at determined microwave frequencies and connected to the microcontroller by an appropriate device allowing to pass from one frequency to another within some microseconds.

I claim:

1. A method for determining a proportion of at least three phases of a multiphase medium flowing in a direction, the multiphase medium comprising at least an aqueous phase, an organic phase and a gaseous phase, the at least three phases having at least one characteristic permitting the proportion of each of the at least three phases to be determined comprising:

(a) irradiating the multiphase medium with an electromagnetic field emitted from an emission source in a direction not parallel to the direction of flow, the electromagnetic field being emitted at at least three frequencies;

(b) measuring at least one elevation fixed with respect of the multiphase medium an amplitude and a phase shift of the electromagnetic field caused by irradiating the multiphase medium with each of the at least three frequencies; and (c) determining the proportion of at least the three phases constituting the multiphase medium for each of the at least three frequencies in response to a comparison of the measured amplitude and the phase shift with stored data.

2. A method in accordance with claim 1 wherein:

the characteristic is permittivity of the medium to the electromagnetic field in a microwave region.

3. A method in accordance with claim 1 wherein:

steps (a)–(c) are carried out at least once for a plurality of different elevations and a distribution of the proportion of the at least three phases is determined from a section of a pipe defined by a direction of irradiation of electromagnetic radiation in a microwave region through the pipe with one side of the pipe extending in a direction which is not parallel to the direction of irradiation of the electromagnetic radiation.

4. A method as recited in claim 1 wherein:

a transmitting antenna is provided comprising a plurality of elements which each are used for irradiating the medium; and a receiving antenna is provided comprising a plurality of elements which measures at at least one elevation fixed with respect to the multiphase medium by scanning each of the plurality of elements in the receiving antenna one after another.

5. A method as recited in claim 1 wherein:

a transmitting antenna comprising a plurality of elements is provided and is used during step (a) and a receiving antenna comprising a plurality of elements is used during step (b) by irradiating the medium with one element of the transmitting antenna followed by scanning a corresponding receiving element of the receiving antenna and repeating the irradiating the medium with another element of the transmitting antenna and repeating the scanning of a corresponding element of the receiving antenna for each pair of transmitting and receiving antenna elements until all of the antenna elements are used.

6. A method in accordance with claim 1 wherein:

a transmitting antenna comprising a plurality of elements and a receiving antenna comprising a plurality of elements is provided and used with step (a) being performed by irradiating the medium from one element of the transmitting antenna and with step (b) being performed by scanning all of the elements of the receiving antenna one after another.

7. A method a recited in claim 1 wherein:

the stored data is determined from a known multiphase fluid having a known phase nature and known proportion.

8. A method in accordance with claim 1 wherein:

the multiphase medium is irradiated with a microwave beam having a frequency ranging between 1 and 8 GHz.

9. A method in accordance with claim 1 wherein:

a velocity of at least one phase of the at least three phase multiphase medium is measured using the Doppler effect by irradiating the medium with one of an electromagnetic field or an ultrasonic wave and a flow rate of at least one of the phases is determined.

10. A method in accordance with claim 1 wherein:

the multiphase medium is a petroleum effluent.

11. A method according to claim 1 wherein step (a) comprises the irradiation of the multiphase medium with a fourth frequency with the proportion of oil and the gaseous phase being determined with the fourth frequency in response to comparison of the measured amplitude and the phase shift with stored data.

12. A method according to claim 11 wherein the first frequency varies between 2.1 to 2.6 GHz, the second frequency varies between 2.6 to 3.15 GHz, the third frequency varies between 3.7 and 4 GHz and fourth frequency varies between 6.1 to 6.3 GHz.

13. A device for determining a proportion of at least there phases of a multiphase medium flowing in a direction, the multiphase medium comprising at least an aqueous phase, an organic phase and a gaseous phase, the phases having at least one characteristic permitting the proportion of each of the at least three phases to be determined comprising:

(a) means for emitting an electromagnetic field at at least three frequencies which crosses through the multiphase medium flowing in the pipe in a direction not parallel to the direction of flow;

(b) means, coupled to the means for emitting, for producing the at least three frequencies;

(c) means for receiving the electromagnetic field after the crossing through the multiphase medium for each of the at least three frequencies and for producing a measurement of an amplitude and a phase shift of the electromagnetic field caused by passing through the medium for each of the at least three frequencies; and (d) processing and control means for determining directly from the determined amplitude and phase shift the proportion of at least the gaseous phase, the organic phase and the aqueous phase.

14. A device as recited in claim 13 further comprising:

a microwave transparent window which is part of the pipe; and wherein the means for emitting and the means for receiving are wide band antennas each comprising a plurality of separated elements with the elements of each of the means for emitting and means for receiving being separated by a first material; and a second material is disposed between the antennas and the microwave transparent window which is part of the pipe with the first and second materials having a dielectric characteristic permitting the wide band antennas to be optimized to a relative permittivity variation between the phases of the multiphase medium.

15. A device as recited in claim 14 wherein:

the first material is an epoxy resin and the second material is a ceramic material withstanding a temperature of 100° C. and a pressure of 100 bars.

16. A device as recited in claim 13 further comprising:

means for measuring velocity of at least one phase of the multiphase fluid flowing in the pipe.

17. A device in accordance with claim 13 wherein:

the multiphase medium is a petroleum effluent.

18. A device according to claim 13 wherein the means of step (b) emits a fourth frequency with a proportion of the gaseous phase and the organic phase being determined with the fourth frequency in response to comparison of the determined amplitude and phase shift.

19. A device of claim 18 wherein the first frequency varies between 2.1 to 2.6 GHz, the second frequency varies between 2.6 to 3.15 GHz, the third frequency varies between 3.7 and 4 GHz and fourth frequency varies between 6.1 to 6.3 GHz.

\* \* \* \* \*